(12) United States Patent
Dahmen et al.

(10) Patent No.: US 7,960,591 B2
(45) Date of Patent: *Jun. 14, 2011

(54) METHOD FOR PRODUCING TRIETHYLENETETRAMINE

(75) Inventors: Kirsten Dahmen, Freinsheim (DE); Alfred Oftring, Bad Dürkheim (DE); Randolf Hugo, Dirmstein (DE); Katrin Baumann, Mannheim (DE); Thilo Hahn, Kirchheimbolanden (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/529,034

(22) PCT Filed: Feb. 27, 2008

(86) PCT No.: PCT/EP2008/052338
§ 371 (c)(1), (2), (4) Date: Aug. 28, 2009

(87) PCT Pub. No.: WO2008/104553
PCT Pub. Date: Sep. 4, 2008

(65) Prior Publication Data
US 2010/0029991 A1    Feb. 4, 2010

(30) Foreign Application Priority Data

Mar. 1, 2007 (EP) .................................... 07103286

(51) Int. Cl.
*C07C 209/48* (2006.01)
(52) U.S. Cl. ........................ 564/491; 564/490
(58) Field of Classification Search ............ 564/491
See application file for complete search history.

(56) References Cited

U.S. PATENT DOCUMENTS

| 3,462,493 A | 8/1969 | Coker et al. |
| 4,146,560 A | 3/1979 | Larkin et al. |
| 4,235,821 A | 11/1980 | Butte, Jr. et al. |
| 5,030,740 A | 7/1991 | Bowman et al. |
| 5,530,127 A | 6/1996 | Reif et al. |
| 6,297,394 B1 | 10/2001 | Voit et al. |
| 6,469,211 B2 | 10/2002 | Ansmann et al. |
| 6,518,449 B1 | 2/2003 | Boschat et al. |
| 6,852,669 B2 | 2/2005 | Voit et al. |
| 7,091,153 B2 | 8/2006 | Voit et al. |
| 2002/0058842 A1 | 5/2002 | Ansmann et al. |
| 2006/0041170 A1 | 2/2006 | Jonas et al. |

FOREIGN PATENT DOCUMENTS

| DE | 2755687 A1 | 8/1978 |
| DE | 3003729 A1 | 8/1980 |
| DE | 68911508 T2 | 3/1994 |
| EP | 0222934 A1 | 9/1985 |
| EP | 0212986 A1 | 3/1987 |
| EP | 0382508 A2 | 8/1990 |
| EP | 0696572 A1 | 2/1996 |
| EP | 0963975 A1 | 12/1999 |
| EP | 1209146 A1 | 5/2002 |
| EP | 0913388 B1 | 10/2003 |
| EP | 1742045 A1 | 1/2007 |
| WO | WO-9933561 A1 | 7/1999 |
| WO | WO-99/44984 | 9/1999 |

OTHER PUBLICATIONS

Nishimura, Shigeo, "Handbook of Heterogeneous Catalytic Hydrogenation for Organic Synthesis", (2001) pp. 213-215.
Malveda, Michael P., "CEH Product Review: Ethyleneamines"; SRI Report, SRI International, (2003), pp. 1-53.
Gamage, Swarna A., et al., "Dicationic Bis(9-methylphenazine-1-carboxamides): Relationships between Biological Activity and Linker Chain Structure for a Series of Potent Topoisomerase Targeted Anticancer Drugs", J. Med., Chem, (2001), vol. 44, pp. 1407-1415.
U.S. Appl. No. 12/529,101, filed Aug. 28, 2009.
U.S. Appl. No. 12/529,096, filed Aug. 28, 2009.
U.S. Appl. No. 12/529,047, filed Aug. 28, 2009.
U.S. Appl. No. 12/529,072, filed Aug. 28, 2009.
U.S. Appl. No. 12/529,079, filed Aug. 28, 2009.
U.S. Appl. No. 12/529,087, filed Aug. 28, 2009.
U.S. Appl. No. 12/529,107, filed Aug. 28, 2009.
Li, et al., "The Synthesis of Cyclic Spermine Alkaloids: Analogues of Buchnerine and Budmunchiamine C", Helvetica Chimica Acta, vol. 86, (2003), pp. 310-323.

*Primary Examiner* — Brian J Davis
(74) *Attorney, Agent, or Firm* — Connolly Bove Lodge & Hutz LLP

(57) ABSTRACT

The invention relates to a process for preparing triethylenetetramine (TETA), which comprises hydrogenating ethylenediaminediacetonitrile (EDDN) in the presence of a catalyst and a solvent.

14 Claims, No Drawings

METHOD FOR PRODUCING TRIETHYLENETETRAMINE

CROSS-REFERENCE TO RELATED APPLICATIONS

This application is a national stage application (under 35 U.S.C. §371) of PCT/EP2008/052338, filed Feb. 27, 2008, which claims benefit of European application 07103286.6, filed Mar. 1, 2007.

BACKGROUND OF THE INVENTION

The invention relates to a process for preparing triethylenetetramine (TETA) by hydrogenation of ethylenediaminediacetonitrile (EDDN) over a catalyst. If appropriate, EDDN can also be present as a constituent of an amino nitrile mixture which additionally comprises ethylenediaminemonoacetonitrile (EDMN).

It is generally known that aliphatic nitrites, which may be substituted by further functional groups, can be hydrogenated in the presence of catalysts to form the corresponding amines. As indicated below, such hydrogenation processes are also known for various amino nitrites for producing some amines. However, it has up to the present not been stated anywhere that TETA can also be prepared from the amino nitrite EDDN or, if appropriate, from an amino nitrite mixture comprising EEDN and EDMN by direct hydrogenation of the amino nitrile. The processes known hitherto for preparing TETA are, however, as indicated below, associated with disadvantages.

Numerous processes for hydrogenating the α-amino nitrites aminoacetonitrile (AAN) and iminodiacetonitrile (IDAN) or β-amino nitrites have been described in the prior art. Thus, it is known that the hydrogenation of β-amino nitrites generally proceeds without problems, while the hydrogenation of α-amino nitriles is associated with the occurrence of numerous disadvantages such as hydrogenolysis of the C—CN bond or the $R_2N$—C bond. "Handbook of Heterogeneous Catalytic Hydrogenation for Organic Synthesis, pp. 213 to 215" indicates the problems of the hydrogenation of α-amino nitrites for the example of α-alkylamino nitrites or cyclic α-amino nitrites compared to β-amino nitrites. The known stability problems of α-amino nitrites are presumably the main reason why to the present day only the hydrogenation of the α-amino nitrites AAN or IDAN to EDA (ethylenediamine) or DETA (diethylenetriamine), respectively, has been described in detail. However, EDA or DETA are prepared industrially by means of the EDC or MEOA process described below. However, a corresponding hydrogenation is not known for higher α-amino nitrites.

DE-A 3 003 729 describes a process for hydrogenating aliphatic nitrites, alkyleneoxy nitrites and alkylene amino nitrites to primary amines of a cobalt or ruthenium catalyst in the presence of a solvent system. The solvent system used comprises water and ammonia together with an ether or polyether. The alkylene amino nitrites or alkylene oxy nitrites which can be used as starting materials are in each case defined by means of a complex general formula. As specific compounds or examples which can be hydrogenated to the corresponding diamine, mention is made of, inter alia, ethylenediaminedipropionitrile (EDDPN; also referred to as N,N'-bis(cyanoethyl)-ethylenediamine) or 3,3'-(ethylenedioxy) dipropionitrile. On the other hand, DE-A 3 003 729 does not make any reference to the use of individual compounds of EDA derivatives having cyanomethyl substituents, e.g. EDDN or EDMN. In addition, EDMN does not come within the general definition of alkylene amino nitrites according to this document.

EP-A 0 382 508 describes a process for the batchwise preparation of acyclic, aliphatic polyamines by hydrogenation of acyclic, aliphatic polynitriles in the liquid phase over Raney cobalt catalysts, preferably in the presence of anhydrous ammonia. Here, a polynitrile solution is fed into a reaction zone which comprises the Raney cobalt catalyst in an essentially oxygen-free atmosphere. During the entire time of the reaction, the polynitrile solution is fed in at a rate which is not greater than the maximum rate at which the polynitrile reacts with the hydrogen in the reaction zone. This process enables polyamines to be prepared from polynitriles such as iminodiacetonitrile (IDAN), nitrilotriacetonitrile, ethylenediaminetetraacetonitrile (EDTN) or further compounds which have 2 or more cyano groups and are not specified in more detail.

EP-A 212 986 relates to a further process in which the same aliphatic polynitriles as in EP-A 0 382 508 can be hydrogenated to the corresponding polyamines under a granular Raney cobalt catalyst in the presence of a liquid primary or secondary amine comprised in the feed stream. As amino components which have to be present, mention is made of, inter alia, ethylenediamine (EDA) and also numerous further primary or secondary amines.

EP-A 1 209 146 relates to a further process for the continuous hydrogenation of nitrites to primary amines, in which the respective nitrites are used in the liquid phase over a suspended, activated Raney catalyst based on an aluminum alloy and the reaction is carried out in the absence of ammonia and basic alkali metal or alkaline earth metal compounds. Nitriles which can be converted into the corresponding ethylene amines include, among many others, IDAN, EDTN, EDDPN or ethylenediaminemonopropionitrile (EDMPN).

EP-B 0 913 388 relates to a process for the catalytic hydrogenation of nitriles, which comprises contacting the nitrile with hydrogen in the presence of a cobalt sponge catalyst under conditions for carrying out the conversion of the nitrile groups into the primary amine. The cobalt sponge catalyst has been treated beforehand with a catalytic amount of lithium hydroxide and the process is carried out in the presence of water. Suitable nitrites are aliphatic nitrites having from 1 to 30 carbon atoms, including, inter alia, β-amino nitrites such as dimethylaminopropionitrile. A further process for preparing polyamines from the corresponding polynitriles is disclosed in DE-A 27 55 687. In this process, the hydrogenation is carried out over a pelletized hydrogenation catalyst in the presence of a stabilizer which inhibits decomposition of the catalyst. As polynitrile, it is possible to use, inter alia, ethylenediaminedipropionitrile (EDDPN). Suitable stabilizers include, inter alia, EDA.

US-A 2006/0041170 relates to a process for preparing TETA, in particular TETA salts, and their use as drugs. In this multistage process, EDDN is prepared first. EDDN is subsequently reacted with benzaldehyde to form a (cyclic) imidazolidine derivative. This cyclic compound, which has two cyano groups, is reduced, for example by reaction with hydrogen, to give the corresponding cyclic diamino compound. This diamino compound is in turn hydrolyzed in the presence of an acid to give the corresponding TETA salt. In an alternative embodiment, the cyclic diamine compound is likewise reacted with benzaldehyde to form the corresponding diimine compound which is subsequently once again hydrolyzed in the presence of an acid to give the corresponding TETA salt. As further process alternatives, this document describes the reaction of EDDN with Boc protective groups (tert-butoxycarbonyl groups). The resulting EDDN derivative protected by two Boc protective groups is subsequently hydrogenated to give the corresponding protected TETA derivative. The Boc protective groups are removed by acid hydrolysis to give the corresponding TETA salt. A disadvantage of the process described in US-A 2006/0041170 is, in particular, that it is a multistage hydrogenation process in which the starting material EDDN used firstly has to be chemically derivatized in order to carry out the hydrogenation. A further disadvantage is that TETA is initially obtained as salt but not in the free base form.

There is therefore no report anywhere in the prior art that EDDN or amino nitrile mixtures comprising EDDN or EDMN can be used for preparing TETA and, if appropriate, further ethylene amines by direct hydrogenation of the amino nitrile. However, other (industrial) processes for preparing TETA are known.

EP-A 222 934 relates to a process for preparing higher alkylenepolyamines by reaction of a vicinal dihaloalkane with an excess of ammonia in the aqueous phase with addition of a strong base, resulting in formation of an imine intermediate which is subsequently reacted with an alkylenepolyamine to form the higher alkylenepolyamine. A suitable vicinal dihaloalkane is, in particular, ethylene dichloride (EDC or 1,2-dichloroethane). Alkylenepolyamines used are, in particular, ethylenediamine or higher ethylene amines such as DETA and also TETA and tetraethylenepentamine (TEPA). These processes (EDC processes) give a mixture of various ethylene amines (linear ethylene amines such as EDA, DETA, TETA, TEPA or higher ethylene amines and also cyclic derivatives such as piperazine (Pip) or aminoethylpiperazine (AEPip)). Depending on the ethylene amine added to the starting materials EDC and $NH_3$, the reaction mixture comprises a corresponding proportion of higher ethylene amines. If, for example, TEPA is to be specifically prepared, the ethylene amine TETA is added to the starting materials EDC and $NH_3$. As a result, the product (ethylene amine mixture) comprises a relatively high proportion of TEPA, but also the abovementioned further linear and cyclic ethylene amines. Disadvantages of this process are, in particular, that the process proceeds with low selectivity (to the components of the ethylene amine mixture obtained) and that a specific ethylene amine (for example DETA) firstly has to be prepared and is subsequently introduced into the process to prepare the next higher ethylene amine (for example TETA) in a targeted manner or to increase the obtained yield. However, this process represents a corrosion problem because of the starting materials used (haloalkanes) and the hydrochloric acid formed and also an environmental problem because of the salts formed.

U.S. Pat. No. 3,462,493 relates to a process for preparing TETA, in which an at least five-fold molar excess of EDA is reacted with ethylene dichloride or ethylene dibromide. By-products obtained here are, in particular, Pip or piperazinoethylethylenediamine.

DE-T 689 11 508 describes an alternative process for preparing linearly extended polyalkylenepolyamines such as TEPA. In this process, a bifunctional aliphatic alcohol is reacted with an amine reactant in the presence of a tungsten-comprising catalyst. A suitable bifunctional aliphatic alcohol is, in particular, monoethanolamine (MEOA), an EDA or DETA, for example, can be used as amine reactants. This process in principle gives mixtures of linearly extended poly-alkylenepolyamines (i.e. ethylene amine mixtures). These ethylene amine mixtures comprise DETA, TETA, TEPA, Pip, AEPip or piperazine derivatives of higher ethylene amines with the proportion of the respective components varying according to the amine reactants used. If DETA is used as amine reactant, an ethylene amine mixture having a high proportion of TETA and TEPA is obtained. Disadvantages of this process are that the process proceeds with low selectivity (to the components of the ethylene amine mixture obtained) and that an additional ethylene amine firstly has to be synthesized and then reacted with the bifunctional aliphatic alcohol (for example MEOA). This forms relatively large amounts of by-products such as aminoethylethanolamine (AEEA) or higher hydroxy-comprising ethylene amines which are of little economic interest. The relatively large amount of by-products obtained is due to the fact that MEOA or the higher ethanolamines (e.g. AEEA) can react with themselves instead of with the amine used. Owing to the (statistically) many reaction possibilities, the selectivity to the linear TETA is quite low because of the coproducts and cannot be controlled. The synthesis can be carried out only at a partial conversion.

A review of the preparation of ethylene amines is given by the SRI report "CEH Product Review Ethyleneamines"; SRI International, 2003; pp. 1-53, in which EDA or DETA, in particular, are prepared by the above-described processes (using the starting materials EDC or MEA). Here, higher ethylene amines such as TETA or TEPA are formed as by-products or are obtained in relatively high yield by further reaction of the starting materials with EDA or DETA.

BRIEF SUMMARY OF THE INVENTION

It is therefore an object of the present invention to provide a simple and inexpensive process for preparing TETA and, if appropriate, DETA in a targeted manner.

This object is achieved by a process for preparing triethylenetetramine (TETA), which comprises hydrogenating ethylenediaminediacetonitrile (EDDN) in the presence of a catalyst and a solvent. If EDDN is present in an amino nitrile mixture comprising at least 30% by weight of EDDN and at least 5% by weight of ethylenediaminemonoacetonitrile (EDMN), DETA is obtained as further main product in addition to TETA. For the purposes of the present invention, hydrogenation is reaction of EDDN or, if appropriate, further amino nitrites with hydrogen.

DETAILED DESCRIPTION OF THE INVENTION

The process of the invention has the advantage that TETA and, if appropriate, the further main component DETA can be prepared with a high conversion and/or selectivity. The increased selectivity is reflected in the fact that, in particular, the EDDN used is hydrogenated predominantly to TETA. The by-products formed are mainly further linear ethylene amines such as DETA or TEPA. The proportion of cyclic ethylene amines such as AEPip is relatively small in the process of the invention. However, some of the further ethylene amines are likewise interesting products of value (mainly the linear ethylene amines such as DETA) whose isolation is worthwhile, for example in industrial processes. On the other hand, cyclic ethylene amines such as AEPip are of relatively little interest as product of value. However, AEPip can be recirculated to the amino nitrile synthesis and after subsequent hydrogenation likewise gives a product of value which is also referred to as "technical-grade TETA".

EDDN and, if appropriate, EDMN are advantageously reacted completely or virtually completely. This is particularly important in industrial processes since unreacted starting material generally has to be recirculated to the product circuit or be disposed of. Processes in which relatively large amounts of EDDN and/or EDMN are not reacted are particularly disadvantageous because of the high instability of EDDN and EDMN. Firstly, both EDDN and EDMN tend to decompose at relatively high temperatures, so that the decomposition products cannot be recirculated to the respective circuit, and secondly this decomposition can also proceed with explosive vigor. Since the amino nitrites can be reacted completely in the process of the invention, no efforts have to be made to recirculate them to the production cycle.

A further advantage of the process of the invention is that, in contrast to the EDC process, the use of chlorinated hydrocarbons as starting material can be dispensed with. In addition, no hydrochloric acid or salts thereof is/are obtained as further reaction product. The disposal of the abovementioned substances is, particularly in the case of industrial processes, an (environmental) problem. An advantage compared to the MEOA process is that the formation of AEEA and further compounds having a hydroxy function does not play a role because of the different starting materials.

If an amino nitrite mixture is hydrogenated in the process of the invention, it is an advantage that, depending on the requirements of the market, a larger or smaller proportion of TETA or DETA can be prepared. This is because the ratio of the starting materials EDMN to EDDN is in principle reflected in the ratio of DETA to TETA in the product. Thus, specific amino nitrite mixture compositions can be used in a targeted manner in the process of the invention in order to serve the ratios of quantities required in the market. The process of the invention gives, in high selectivity, an ethylene amine mixture which comprises at least 30% of TETA together with at least 5% of DETA and, if appropriate, further ethylene amines such as piperazine derivatives as products of value.

In one embodiment, EDDN is used as (main) starting material in the process of the invention. In this embodiment, the content of further amino nitrites in the solution which is hydrogenated is preferably limited to ≦10% by weight, in particular ≦5% by weight, based on EDDN. In a further embodiment of the present invention, EDDN is present as a constituent of an amino nitrile mixture. The amino nitrite mixture comprises at least 30% by weight (percent by weight) of EDDN, at least 5% by weight of ethylenediaminemonoacetonitrile (EDMN) and also, if appropriate, further amino nitrites. The amino nitrite mixture normally comprises from 30 to 95% by weight, preferably from 50 to 95% by weight, particularly preferably from 75 to 90% by weight, of EDDN. The amino nitrite mixture normally comprises from 5 to 70% by weight, preferably from 5 to 50% by weight, of EDMN. It particularly preferably comprises from 10 to 25% by weight of EDMN. The above percentages by weight of EDDN and EDMN and of the further amino nitrites are based on the total amount of the amino nitrites comprised in the mixture. Any water or other solvents which are additionally present are not taken into account in these amounts.

In general, any type/grade of EDDN and, if appropriate, of EDMN and further amino nitrites can be used. The respective amino nitrites are preferably used in the form of their aqueous solution. Processes for preparing EDDN or EDMN are known to those skilled in the art; see K. Masuzawa et al., Bull. Chem. Soc. Japan, Volume 41 (1968), pages 702-707; H. Brown et al., Helvetica Chimica Acta, Volume 43 (1960), pages 659-666 and H. Baganz et al., Chem. Ber., 90 (1957), pages 2944-2949. EDDN and/or EDMN are preferably prepared by reaction of EDA and formaldehyde cyanohydrin (FACH). Processes for preparing FACH are known to those skilled in the art.

Furthermore, EDDN and/or EDMN can be prepared by reaction of EDA with formaldehyde and hydrocyanic acid.

EDDN can in principle be purified by methods known to those skilled in the art before use in the process of the invention. If appropriate, freshly prepared EDDN can also be used in the process of the invention. Purification steps can be carried out after the EDDN synthesis; removal of water from the EDDN prepared is conceivable. If EDDN is used in an amino nitrile mixture comprising EDDN and EDMN in the process of the invention, the individual components of this amino nitrile mixture can be synthesized separately and combined in the appropriate amounts to form the amino nitrile mixture before use in the process of the invention.

In a preferred embodiment of the present invention, EDDN and EDMN are synthesized together. EDDN and EDMN are preferably prepared by reaction of EDA and FACH. The ratio of EDDN to EDMN in the amino nitrile mixture can be set via the concentration of FACH. The molar ratio of EDA to FACH is preferably from 1:1.5 to 1:2 [mol/mol]. The smaller the proportion of FACH, the higher the proportion of EDMN in the amino nitrile mixture. Preference is given to preparing an amino nitrile mixture having the above concentrations of EDDN and EDMN. The concentration of EDDN or EDMN in the amino nitrile mixture obtained can be increased or decreased by appropriate addition.

In an embodiment of the present invention, the low boilers are separated off from the EDDN starting material which may further comprise EDMN before the hydrogenation. Preference is given to using EDDN, which may comprise EDMN, which is largely free of low boilers in the process of the invention. If FACH is used for the preparation of EDDN and, if appropriate, EDMN, the removal of low boilers can be carried out before the reaction of FACH with EDA. Preference is given to separating off hydrocyanic acid (HCN) as low boiler. HCN can also occur as decomposition product of FACH. Furthermore, any ammonia present can be separated off at this point. The removal is preferably carried out by distillation, for example in the form of a thin film evaporation such as a Sambay distillation ("Chemie Ingenieur Technik, Vol. 27, pp. 257-261). If appropriate, the reaction mixture can also be stripped by means of nitrogen before the hydrogenation.

EDDN is a solid at room temperature, as is EDMN. The hydrogenation of the process of the invention is consequently carried out in the presence of a solvent such as an organic solvent and/or water. Preference is given to using water as solvent, and mixtures of water and organic solvents such as ethers, in particular THF, or alcohols, in particular methanol, can also be used if appropriate. The additional use of an organic solvent (i.e. an inert organic compound) in addition to water has been found to be advantageous since stabilization of the individual components of the aqueous amino nitrile mixture, in particular in the presence of the resulting amines, can be achieved in this way. In addition, a rinsing effect (reduction of rinsing cycles, reduction in the discharge of catalyst) on the catalyst used can be achieved by the use of organic solvents, as a result of which its operational life is increased or its consumption is reduced (longer catalyst life) and the space velocity over the catalyst can be improved. The use of suitable solvents can also reduce the formation of alkylated by-products such as AEPip.

A suitable solvent, which can comprise one or more components, should preferably have the following properties:
(a) the solvent should have a stabilizing effect, in particular in the presence of the products, on EDDN or, if appropriate, EDMN, in particular prevent its decomposition at the prevailing temperatures;
(b) the solvent should have a good solvent capability for hydrogen;

(c) the solvent should be inert under the reaction conditions;
(d) the reaction mixture (EDDN, if appropriate water or organic solvent) should form a single phase under the reaction conditions;
(e) the solvent should be selected with a view to a preferred separation of the product from the product stream by distillation after the hydrogenation and separations which are energy-consuming or complicated in terms of apparatus (e.g. close-boiling mixtures or azeotropes which are difficult to separate) should be avoided.
(f) the solvent should be able to be readily separated from the products, i.e. the boiling point should be sufficiently different from those of the products. Here, a boiling point lower than those of the products is preferred.

Possible solvents (apart from water) are organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines such as EDA or ethylamines, esters such as methyl acetate or ethyl acetate and ethers such as diisopropyl ether, diisobutyl ether, glycol dimethyl ether, diglycol dimethyl ether, dioxane and tetrahydrofuran (THF). Ethers are preferably used in the process of the invention, more preferably cyclic ethers and particularly preferably tetrahydrofuran. In a further preferred embodiment, alcohols, in particular methanol, are used as organic solvent.

The solvent is used in a weight ratio to the amino nitrile used (EDDN and, if appropriate, EDMN) of from 0.1:1 to 15:1. The concentration of the amino nitrile mixture in the solution in which the hydrogenation is carried out should be selected so that a suitable feed rate or residence time can be set. Preference is given to mixing amino nitrile in an amount of from 10 to 50% by weight with the solvent. Based on the particularly preferred solvents methanol and tetrahydrofuran, it is advantageous, for example, to use the amino nitrile in an amount of from 20 to 40% by weight based on the solvent.

If water is present, the proportion by weight of water in the solution is in the range from 0 to 70%, preferably from 10 to 50%. The amounts of water indicated are based on the amino nitrile/water mixture.

If appropriate, additional additives can be comprised in the solution in which the hydrogenation is carried out. Possible additives are principally hydroxides such as alkali metal hydroxides, alkoxides, amides, amines. Preferred additives are amines, preferably EDA, and ammonia, in particular EDA. Furthermore, acidic additives such as silicates can additionally be comprised in the solution. These substances can be added as pure substance or as a solution in a solvent. The process of the invention is preferably carried out with addition of additives.

As catalysts for the hydrogenation of the nitrile function to the amine, it is possible to use catalysts which comprise one or more elements of transition group 8 of the Periodic Table (Fe, Co, Ni, Ru, Rh, Pd, Os, Ir, Pt), preferably Fe, Co, Ni, Ru or Rh, particularly preferably Co or Ni, as active species. These include skeletal catalysts (also referred to as Raney® type; hereinafter also Raney catalyst) which are obtained by leaching (activation) of an alloy of hydrogenation-active metal and a further component (preferably Al). The catalysts can additionally comprise one or more promoters. In a preferred embodiment, Raney catalysts, preferably Raney cobalt or Raney nickel catalysts and particularly preferably Raney cobalt catalysts doped with at least one of the elements Cr, Ni or Fe or Raney nickel catalysts doped with one of the elements Mo, Cr or Fe, are used in the process of the invention.

The catalysts can be used as all-active catalysts or in supported form. Supports employed are preferably metal oxides such as $Al_2O_3$, $SiO_2$, $ZrO_2$, $TiO_2$, mixtures of metal oxides or carbon (activated carbons, carbon blacks, graphite).

The oxidic catalysts are activated by reduction of the metal oxides in a hydrogen-comprising gas stream at elevated temperature either outside the reactor or in the reactor before use. If the catalysts are reduced outside the reactor, this can be followed by passivation by means of an oxygen-comprising gas stream or embedding in an inert material in order to avoid uncontrolled oxidation in air and to make safe handling possible. As inert material, it is possible to use organic solvents such as alcohols or else water or an amine, preferably the reaction product. An exception in the activation is the skeletal catalysts which can be activated by leaching with aqueous base, as described in, for example, EP-A 1 209 146.

Depending on the process carried out (suspension hydrogenation, fluidized-bed process, fixed-bed hydrogenation), the catalysts are used as powder, crushed material or shaped bodies (preferably extrudates or pellets).

Particularly preferred fixed-bed catalysts are the all-active cobalt catalysts doped with Mn, P and alkali metal (Li, Na, K, Rb, Cs) which are disclosed in EP-A 742 045. The active catalyst composition of these catalysts before reduction with hydrogen comprises from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, whose catalytically active composition before treatment with hydrogen comprises from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum, for example the catalyst A disclosed in this document which has the composition 33% by weight of Zr, calculated as $ZrO_2$, 28% by weight of Ni, calculated as NiO, 11% by weight of Cu, calculated as CuO, and 28% by weight of Co, calculated as CoO.

Further suitable catalysts are those disclosed in EP-A 696 572, whose catalytically active composition before reduction with hydrogen comprises from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$; for example the catalyst specifically disclosed in this document which has the composition 31.5% by weight of $ZrO_2$, 50% by weight of NiO, 17% by weight of CuO and 1.5% by weight of $MoO_3$. Further suitable catalysts are those described in WO-A-99/44984, which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight based on (a) of a compound based on an alkali metal and/or alkaline earth metal and (d) from 0.001 to 1% by weight based on (a) manganese.

Suspension processes are preferably carried out using Raney catalysts. In the case of Raney catalysts, the active catalyst is produced as "metal sponge" from a binary alloy (nickel, iron, cobalt with aluminum or silicon) by leaching out of one component by means of acid or alkali. Residues of the original alloying component often have a synergistic action.

The Raney catalysts used in the process of the invention are preferably produced from an alloy of cobalt or nickel, particularly preferably cobalt, and a further alloying component which is soluble in alkalis. Aluminum is preferably used as this soluble alloying component, but it is also possible to use other components such as zinc and silicon or mixtures of such components.

To activate the Raney catalyst, the soluble alloying component is completely or partly extracted with alkali, for which purpose it is possible to use, for example, aqueous sodium hydroxide. The catalyst can then be washed with, for example, water or organic solvents.

Individual or a plurality of further elements can be present as promoters in the catalyst. Examples of promoters are metals of transition groups IB, VIB and/or VIII of the Periodic Table, e.g. chromium, iron, molybdenum, nickel, copper, etc.

The activation of the catalysts by leaching of the soluble component (typically aluminum) can be carried out either in the reactor itself or before introduction into the reactor. The preactivated catalysts are air sensitive and pyrophoric and are therefore generally stored and handled under a medium such as water, an organic solvent or a substance which is present in the reaction according to the invention (solvent, starting material, product) or embedded in an organic compound which is solid at room temperature.

According to the invention, in a preferred embodiment use is made of a skeletal Raney cobalt catalyst which has been obtained from a Co/Al alloy by leaching with aqueous alkali metal hydroxide solution, e.g. sodium hydroxide, and subsequent washing with water and preferably comprises at least one of the elements Fe, Ni, Cr as promoters.

Such catalysts typically comprise cobalt together with 1-30% by weight of Al, particularly preferably 2-12% by weight of Al, very particularly preferably 3-6% by weight of Al, 0-10% by weight of Cr, particularly preferably 0.1-7% by weight of Cr, very particularly preferably 0.5-5% by weight of Cr, in particular 1.5-3.5% by weight of Cr, 0-10% by weight of Fe, particularly preferably 0.1-3% by weight of Fe, very particularly preferably 0.2-1% by weight of Fe, and/or 0-10% by weight of Ni, particularly preferably 0.1-7% by weight of Ni, very particularly preferably 0.5-5% by weight of Ni, in particular 1-4% by weight of Ni, with the percentages by weight in each case being based on the total weight of the catalyst.

As catalyst in the process of the invention, use can advantageously be made of, for example, a skeletal cobalt catalyst "Raney 2724" from W.R. Grace & Co. This catalyst has the following composition:
Al: 2-6% by weight, Co: $\geq$86% by weight, Fe: 0-1% by weight, Ni: 1-4% by weight, Cr: 1.5-3.5% by weight.

It is likewise possible to use a skeletal nickel catalyst which has been obtained from an Ni/Al alloy by leaching with aqueous alkali metal hydroxide solution, e.g. sodium hydroxide, and subsequent washing with water and preferably comprises at least one of the elements Fe, Cr as promoters for the purposes of the invention.

Such catalysts typically comprise nickel together with 1-30% by weight of Al, particularly preferably 2-20% by weight of Al, very particularly preferably 5-14% by weight of Al,
0-10% by weight of Cr, particularly preferably 0.1-7% by weight of Cr, very particularly preferably 1-4% by weight of Cr, and/or
0-10% by weight of Fe, particularly preferably 0.1-7% by weight of Fe, very particularly preferably 1-4% by weight of Fe,
with the percentages by weight in each case being based on the total weight of the catalyst.

As catalyst in the process of the invention, use can advantageously be made of, for example, a skeletal nickel catalyst A 4000 from Johnson Matthey.

This catalyst has the following composition
Al: $\leq$14% by weight, Ni: $\geq$80% by weight, Fe: 1-4% by weight, Cr: 1-4% by weight.

In the case of decreasing activity and/or selectivity of the catalysts, they can be regenerated by methods known to those skilled in the art, as disclosed, for example, in WO 99/33561 and the documents cited therein.

The regeneration of the catalyst can be carried out in the actual reactor (in situ) or on the catalyst which has been removed from the reactor (ex situ). In the case of fixed-bed processes, regeneration is preferably carried out in situ; in the case of suspension processes, part of the catalyst is preferably taken continuously or discontinuously from the reactor, regenerated ex situ and returned.

The temperatures at which the process of the invention is carried out are in the range from 40 to 150° C., preferably from 70 to 140° C., in particular from 80 to 130° C.

The pressure prevailing in the hydrogenation is generally in the range from 5 to 300 bar, preferably from 30 to 250 bar, particularly preferably from 40 to 160 bar.

In a preferred embodiment, EDDN or the amino nitrile mixture comprising EDDN is fed to the hydrogenation at a rate which is not greater than the rate at which the EDDN and, if applicable, the other components of the amino nitrile mixture react with hydrogen in the hydrogenation.

The feed rate is preferably set so that effectively quantitative conversion is achieved. This is influenced by temperature, pressure, type of mixture, amount and type of catalyst, the reaction medium, quality of mixing of the contents of the reactor, residence time, etc.

The process of the invention is carried out using a solvent (or a plurality of solvents) which is firstly mixed completely with EDDN or the amino nitrile mixture. The solution obtained, which may, if appropriate, also comprise additives, is subsequently fed into the reaction vessel comprising the catalyst. As an alternative, a partial amount of the solvent can also be introduced into the reaction vessel separately from the solution comprising EDDN, the solvent and, if appropriate, the additive. If appropriate, the additive is introduced separately or else as a solution in the partial amount of the solvent.

If appropriate, EDDN is fed in as an aqueous solution and an organic solvent is fed in separately with or without additive.

If appropriate, for example in the case of semibatch processes, part of the solvent can be placed together with the catalyst in the reaction vessel, whereupon the solution is fed in. The EDDN comprised in the solution and any further amino nitrites such as EDMN comprised therein are normally fed in at a rate which is not greater than the rate at which EDDN reacts with hydrogen in the hydrogenation.

The process of the invention for preparing TETA by hydrogenation of EDDN can be carried out continuously, semicontinuously or batchwise in a fixed-bed, fluidized-bed or suspension mode in customary reaction vessels which are suitable for catalysis. Reaction vessels in which contacting of the amino nitrile and the catalyst with the gaseous hydrogen under pressure is possible are suitable for carrying out the hydrogenation.

The hydrogenation in the suspension mode can be carried out in a stirred reactor, jet loop reactor, jet nozzle reactor, bubble column reactor or in a cascade of identical or different reactors of these types. In the case of hydrogenation over a fixed-bed catalyst, tube reactors but also shell-and-tube reactors are conceivable.

In the case of a fixed-bed catalyst, the amino nitrile is conveyed through the catalyst bed in an upward or downward direction. However, the suspension mode is preferably used in semibatch and preferably continuous operation.

The hydrogenation of the nitrile groups takes place with liberation of heat which generally has to be removed. Heat removal can be effected by means of built-in heat-exchange surfaces, cooling jackets or external heat exchangers in a circuit around the reactor. The hydrogenation reactor or a hydrogenation reactor cascade can be operated in a single pass. As an alternative, a recycle mode of operation in which part of the output from the reactor is recirculated to the reactor inlet, preferably without prior work-up of the recycle stream, is also possible. This enables optimum dilution of the reaction solution to be achieved. In particular, the recycle stream can be cooled in a simple and inexpensive manner by means of an external heat exchanger and the heat of reaction can thus be removed. The reactor can also be operated adiabatically, with the increase in the temperature of the reaction solution being able to be limited by means of the cooled recycle stream. Since the reactor itself then does not have to be cooled, a simple and inexpensive construction is possible. An alternative is a cooled shell-and-tube reactor (only in the case of the fixed bed). A combination of the two modes of operation is also conceivable. Here, a fixed-bed reactor is preferably installed downstream of a suspension reactor.

The process of the invention gives the linear ethylene amine ($C_6$ product) TETA as main product (1st case) and further ethylene amines as secondary components. If an amino nitrile mixture comprising EDDN and EDMN is used in the process of the invention, an ethylene amine mixture comprising the two linear ethylene amines ($C_6$ product and $C_4$ product) TETA and DETA as main components (2nd case) and further ethylene amines as secondary component is obtained.

The secondary components can in both cases be both linear and cyclic ethylene amines or other by-products. In the 1st case, AEPip ($C_6$ (by-)product) is formed as most important cyclic by-product. The ratio of TETA to AEPip in the product is normally in the range from 3:1 to 20:1. This ratio can, for example, be controlled by the choice of the solvent, the catalyst, the amount of water and/or the addition of an additive. In the 1st case, DETA is likewise a (linear) by-product. Further secondary reactions are decomposition reactions, but these can be controlled and minimized by, in particular, choice of the solvent, the addition rate, the starting material purity and/or the catalyst. In the 2nd case, Pip is obtained as further important cyclic by-product ($C_4$ (by-)product) which is formed mainly from EDMN. As regards the formation and control of the ratio of DETA to Pip, what has been said above about the ratio of TETA to AEPip applies. The process of the invention is illustrated in scheme 1 below for the 2nd case, in which EDDN and EDMN are, by way of example, prepared together from FACH.

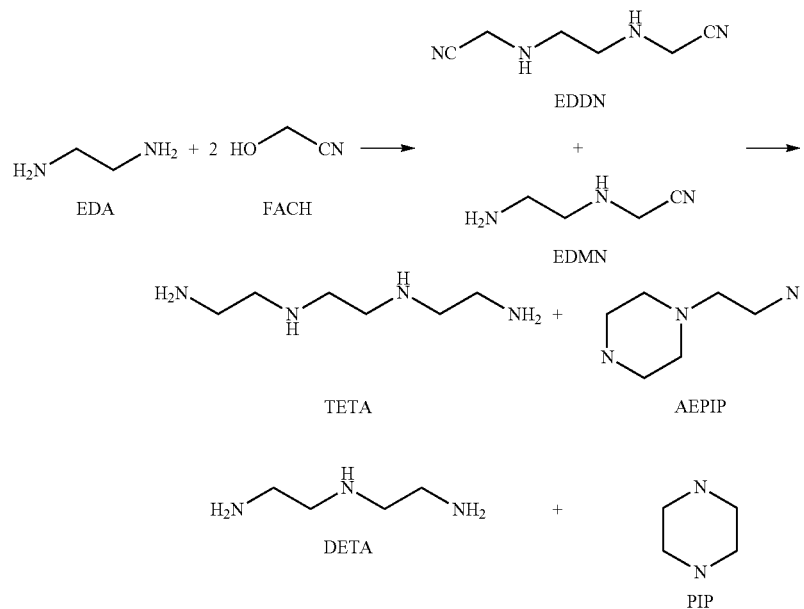

Scheme 1

In the second case, the term "ethylene amine mixture" is used because the reaction product comprises two linear ethylene amines as main components (TETA and DETA), while in the first case only one linear ethylene amine is present as main product (TETA). The by-products mentioned above and below are consequently not taken into account in the definition of terms in these two cases.

In the first case, TETA is obtained in a selectivity of preferably ≧70% by weight, in particular ≧85% by weight, particularly preferably >90% by weight, based on the amount of EDDN used. In the second case, the ratio of the starting materials EDDN and EDMN is in principle reflected in the ratio of the corresponding products TETA and DETA after the hydrogenation.

For the purposes of the present invention, the term "further ethylene amine" refers to any hydrocarbon-comprising compound which is different from TETA (1st case) and from TETA and DETA (2nd case) and comprises at least two ethylene units and at least two functional groups selected from among primary amino groups, secondary amino groups and tertiary amino groups. For the purposes of the present invention, cyclic compounds such as piperazine (Pip) and its derivatives are also encompassed by the term further ethylene amine. Likewise, ethylenediamine (EDA) should be regarded as a further ethylene amine. Further ethylene amines are, in particular, diethylenetriamine (DETA; only 1st case), piperazine (Pip), aminoethylenepiperazine (AEPip) and tetraethylenepentamine (TEPA).

After the hydrogenation, the product obtained (TETA or ethylene amine mixture) can be purified further if appropriate, for example by separating off the solvent and/or the catalyst by methods known to those skilled in the art. In particular, the main products (TETA and, if appropriate, DETA) can be isolated together or individually from the reaction product by methods known to those skilled in the art. If the two main products are isolated together, for example by distillation, they can subsequently be separated into the two individual products. Pure TETA and pure DETA are thus ultimately obtained. Other impurities, by-products or further ethylene amines such as TEPA or Pip can likewise be separated off from the respective product by methods known to those skilled in the art. If appropriate, TETA can also be isolated together with diaminoethylpiperazine or piperazinylethylethylenediamine which are formed in small amounts.

In a preferred embodiment, the process of the invention is carried out using tetrahydrofuran or methanol as solvent. The temperature in the hydrogenation is preferably from 80 to 140° C., and the pressure is preferably from 40 to 120 bar. The hydrogenation is preferably carried out in the presence of EDA and/or, if appropriate, ammonia.

The following examples illustrate the process of the invention. The proportions are given in % by weight unless indicated otherwise. An internal standard, diethylene glycol dimethyl ether (DEGDME), conveyed with the reaction mixture allows quantification of the product by determination of any volatile decomposition products formed. Quantification is effected by means of gas chromatography (GC), with methanol being in each case added to the samples taken in order to homogenize them.

EXAMPLES

General Method for the Synthesis of Formaldehyde Cyanohydrin (FACH)

Variant a)

6000 g (60 mol) of formaldehyde (30%) are placed in a 6 l reaction vessel provided with a propeller stirrer and a pH of 5.5 is set by means of sodium hydroxide solution (1 mol/l). 1661 g (61.2 mol) of hydrocyanic acid are introduced in gaseous form via a heated U-tube below the stirrer over a period of 2.5 hours, with the reaction temperature being maintained at 30° C. and the pH being maintained at 5.5. After stirring for a further 30 minutes, the pH is brought to 2.5 by means of sulfuric acid (50% strength). The corresponding content is determined by Liebig titration.

Variant b)

7000 g (70 mol) of formaldehyde (30%) are placed in a 6 l reaction vessel provided with a propeller stirrer and a pH of 5.5 is set by means of sodium hydroxide solution (1 mol/l). 1938 g (71.4 mol) of hydrocyanic acid are introduced in gaseous form via a U-tube heated to 50° C. below the stirrer over a period of 3 hours, with the reaction temperature being maintained at 30° C. and the pH being maintained at 5.5. After stirring for a further 10 minutes, the pH is brought to 2.5 by means of sulfuric acid (50% strength). To separate off low boilers, in particular hydrocyanic acid, the output from the reaction is subjected to a Sambay distillation (as described in "Chemie Ingenieur Technik, Vol. 27, pp. 257-261) (1 mbar, 30° C.). The corresponding content is determined by Liebig titration and a content of 43-44% or 67% of FACH is set if appropriate by addition of water.

Example 1

Formaldehyde Cyanohydrin

FACH is prepared by variant a) of the general method.

Ethylenediaminediacetonitrile 536.5 g (4 mol) of FACH (42.5%) are placed in a 2 l reaction vessel and 132 g (2.2 mol) of ethylenediamine are added dropwise over a period of 2 hours at a temperature of not more than 35° C. while cooling in ice. The reaction mixture changes color from slightly yellowish through orange to brown. After stirring further for a short time, the free hydrocyanic acid is removed by stripping with nitrogen (Volhard titration). According to Liebig titration, a conversion of FACH of 97.2% is attained.

Triethylenetetramine a) The material obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard and 4.2 g of water in 106 g of THF is fed in over a period of 120 minutes. The reaction mixture is stirred under the reaction conditions for a further 60 minutes. The product mixture is homogenized by means of methanol. The selectivity to AEPip is 28% and that to TETA is 30%. In addition, 4% by weight of C4 products (Pip+DETA) are found.

b) The same material is likewise hydrogenated in a semibatch process. Here, 3.25 g of a Cr-doped Raney cobalt catalyst and also 15 ml of THF and 5.4 g of EDA are placed in a 270 ml autoclave. The autoclave is heated to 120° C. and pressurized with hydrogen to a total pressure of 100 bar. A mixture of 13.8 g of the crude EDDN solution, 13.8 g of an internal standard and 4.2 g of water in 106 g of THF is fed in over a period of 120 minutes. The reaction mixture is stirred under the reaction conditions for a further 60 minutes. The product mixture is homogenized by means of methanol. The selectivity to AEPip is 12% and that to TETA is 43%. In addition, 4% by weight of C4 products (Pip+DETA) are found.

Compared to example 1a, a positive influence of EDA on the formation of TETA is observed.

Example 2

Formaldehyde Cyanohydrin

FACH is prepared by variant b) of the general method.

Ethylenediaminediacetonitrile 132 g (2.2 mol) of EDA are placed in a 2 l reaction vessel and 511.2 g (4 mol) of FACH (44.6%) are added dropwise over a period of 2 hours at a temperature of not more than 30° C. while cooling in ice. After stirring for a further 4.5 hours, the slightly yellowish solution is dispensed. The conversion of FACH is 99.2% according to Liebig titration. The reaction mixture comprises 0.11% of free hydrocyanic acid (determined by Volhard titration). Titration indicates an EDDN yield of 91.7% based on FACH used. EDMN cannot be determined by titration. Assuming that EDMN is formed from reacted ethylenediamine which does not react to form EDDN, the total amino nitrile yield is 95.7% and the yield of EDMN is thus 4%.

Triethylenetetramine a) The material obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard and 4.2 g of water in 106 g of THF is fed in over a period of 120 minutes. The reaction mixture is stirred under the reaction conditions for a further 60 minutes. The product mixture is homogenized by means of methanol. The selectivity to AEPip is 27% and that to TETA is 47%. In addition, 8% by weight of C4 products are detected.

It is found that a significantly better yield of ethylene amines can be achieved by separating off the low boilers after the FACH synthesis. The excess of EPA in the EDDN synthesis results in formation of EDMN which is hydrogenated to the C4 products DETA and Pip.

b) The same material is likewise hydrogenated in a semibatch process. Here, 3.25 g of a Cr-doped Raney cobalt catalyst and also 15 ml of THF and 13.5 g of EDA are placed in a 270 ml autoclave. The autoclave is heated to 120° C. and pressurized with hydrogen to a total pressure of 100 bar. A mixture of 13.8 g of the crude EDDN solution, 13.8 g of an internal standard and 4.2 g of water in 106 g of THF is fed in over a period of 120 minutes. The reaction mixture is stirred under the reaction conditions for a further 60 minutes. The product mixture is homogenized by means of methanol. The selectivity to AEPip is 8% and that to TETA is 82%. In addition, 16% by weight of C4 products are detected.

The addition of EDA in variant 2 b) results in formation of more linear TETA. There is likewise an increase in C4 products due to EDA condensation. The weight increase due to EDA condensation is taken into account in the reported % by weight of the C4 products.

Example 3

Formaldehyde cyanohydrin

FACH is prepared by variant b) of the general method.

Ethylenediaminediacetonitrile 132 g (2.2 mol) of EDA are placed in a 2 l reaction vessel and 340.8 g (4 mol) of FACH (67%) are added dropwise over a period of about 2 hours at a temperature of not more than 30° C. while cooling in ice. After stirring for a further 3 hours, the slightly yellowish solution is dispensed. The conversion of FACH is 99.5% according to Liebig titration. The reaction mixture comprises 0.08% of free hydrocyanic acid (determined by Volhard titration). Titration indicates an EDDN yield of 82.9% based on FACH used. EDMN cannot be determined by titration. Assuming that EDMN is formed from reacted ethylenediamine which does not react to form EDDN, the total amino nitrile yield is 90.5% and the yield of EDMN is thus 8%.

Triethylenetetramine a) The material obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard and 10 g of water in 106 g of THF is fed in over a period of 120 minutes. The reaction mixture is stirred under the reaction conditions for a further 60 minutes. The product mixture is homogenized by means of methanol. The selectivity to AEPip is 10% and that to TETA is 69%. In addition, 13% of C4 products (Pip and DETA) are obtained.

For comparability, more water than in example 2a is added. The excess of EDA in the EDDN synthesis results in formation of EDMN which is hydrogenated to the C4 products DETA and Pip.

b) The material obtained is hydrogenated in a semibatch process. Here, 3.25 g of a Cr-doped Raney cobalt catalyst, 15 ml of THF and 13.5 g of EDA are placed in a 270 ml autoclave. The autoclave is heated to 120° C. and pressurized with hydrogen to a total pressure of 100 bar. A mixture of 13.8 g of the crude EDDN solution, 13.8 g of an internal standard and 10 g of water in 106 g of THF is fed in over a period of 120 minutes. The reaction mixture is stirred under the reaction conditions for a further 60 minutes. The product mixture is homogenized by means of methanol. The selectivity to AEPip is 5% and that to TETA is 76%. In addition, 16% of C4 products are obtained.

The addition of EDA results in formation of more linear TETA. There is likewise an increase in C4 products which is due to EDA condensation.

c) The material obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard in 106 g of THF is fed in over a period of 120 minutes. The reaction mixture is stirred under the reaction conditions for a further 60 minutes. The product mixture is homogenized by means of methanol. The selectivity to AEPip is 9% and that to TETA is 76%. In addition, 12% of C4 products (Pip and DETA) are obtained.

Compared to example 3a, an additional addition of water is omitted, which has a positive effect on TETA.

Example 4

Formaldehyde Cyanohydrin

FACH is prepared by variant b) of the general method.

Ethylenediaminediacetonitrile 132 g (2.2 mol) of EDA are placed in a 2 l reaction vessel and 340.8 g (4 mol) of FACH (67%) are added dropwise over a period of 35 minutes at a temperature of not more than 50° C. while cooling in ice. After stirring for a further 1 hour, the virtually clear solution is dispensed. The conversion of FACH is 99.2% according to Liebig titration. The reaction mixture comprises 0.07% of free hydrocyanic acid (determined by Volhard titration). Titration indicates an EDDN yield of 87.7% based on FACH used. EDMN cannot be determined by titration. Assuming that EDMN is formed from reacted ethylenediamine which does not react to form EDDN, the total amino nitrile yield is 93% and the yield of EDMN is thus 5%.

Triethylenetetramine a) The material obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard in 106 g of THF is fed in over a period of 120 minutes. The reaction mixture is stirred under the reaction conditions for a further 60 minutes. The product mixture is homogenized by means of methanol. The selectivity to AEPip is 10% and that to TETA is 76%. In addition, 11% of C4 products (Pip and DETA) are obtained.

Experiment 4a confirms the results of 3c. Here too, the yield of C4 products (DETA and Pip) is about 11% as a result of the excess of EDA in the EDDN synthesis.

b) The material obtained is hydrogenated in a semibatch process. Here, 3.25 g of a Cr-doped Raney cobalt catalyst, 15 ml of THF and 13.5 g of EDA are placed in a 270 ml autoclave. The autoclave is heated to 120° C. and pressurized with hydrogen to a total pressure of 100 bar. A mixture of 13.8 g of the crude EDDN solution, 13.8 g of an internal standard in 106 g of THF is fed in over a period of 120 minutes. The reaction mixture is stirred under the reaction conditions for a further 60 minutes. The product mixture is homogenized by means of methanol. The selectivity to AEPip is 4% and that to TETA is 80%. In addition, 15% of C4 products are obtained.

Example 4b confirms that hydrogenation in the presence of EDA and a smaller amount of water enables AEPip formation to be significantly suppressed. The content of 15% by weight of C products is usual at the prevailing EDA excess in the EDDN synthesis and also EDA in the hydrogenation.

Example 5

Formaldehyde Cyanohydrin

FACH is prepared by variant b) of the general method.

Ethylenediaminediacetonitrile 180 g (3 mol) of EDA are placed in a 2 l reaction vessel and 511.2 g (6 mol) of FACH (67%) are added dropwise over a period of about 1 hour at a temperature of not more than 50° C. while cooling in ice. After stirring for a further 1.5 hours, the light-yellow solution is dispensed. The conversion of FACH is 99.2% according to Liebig titration. The reaction mixture comprises 0.02% of free hydrocyanic acid (determined by Volhard titration). Titration indicates an EDDN yield of 92.6% based on FACH used. EDMN cannot be determined by titration. Assuming that EDMN is formed from reacted ethylenediamine which does not react to form EDDN, the total amino nitrile yield is 94.5% and the yield of EDMN is thus 2%.

Triethylenetetramine a) The material obtained is hydrogenated in a semibatch process. Here, 3.25 g of a Cr-doped Raney cobalt catalyst and 15 ml of THF are placed in a 270 ml autoclave. The autoclave is heated to 120° C. and pressurized with hydrogen to a total pressure of 100 bar. A mixture of 13.8 g of the crude EDDN solution, 13.8 g of an internal standard in 106 g of THF is fed in over a period of 120 minutes. The reaction mixture is stirred under the reaction conditions for a further 60 minutes. The product mixture is homogenized by means of methanol. The selectivity to AEPip is 10% and that to TETA is 77%. In addition, 3% of C4 products (Pip and DETA) are obtained.

It is found that the use of half-molar amounts of EDA in the EDDN synthesis results in a content of C4 products after the hydrogenation of only 3%.

b) The material obtained is hydrogenated in a semibatch process. Here, 3.25 g of a Cr-doped Raney cobalt catalyst, 15 ml of THF and 13.5 g of EDA are placed in a 270 ml autoclave. The autoclave is heated to 120° C. and pressurized with hydrogen to a total pressure of 100 bar. A mixture of 13.8 g of the crude EDDN solution, 13.8 g of an internal standard in 106 g of THF is fed in over a period of 120 minutes. The reaction mixture is stirred under the reaction conditions for a further 60 minutes. The product mixture is homogenized by means of methanol. The selectivity to AEPip is 6% and that to TETA is 82%. In addition, 7% by weight of C4 products are obtained.

Here too, the content of C4 products is significantly below that in example 4b. The above examples show that the quality of the FACH used has an influence on the reaction time and the color of the product in the production of EDDN. In addition, a higher selectivity is achieved in the subsequent hydrogenation if the FACH is purified by distillation. The addition of an additive also has a positive effect on the selectivity to linear ethylene amines. The amount of water likewise has an influence on the formation of linear TETA.

Example 6

Formaldehyde Cyanohydrin

FACH is prepared by variant b) of the general method.

Ethylenediaminediacetonitrile 132 g (2.2 mol) of EDA are placed in a 2 l reaction vessel and 340.8 g (4 mol) of FACH (67%) are added dropwise over a period of 35 minutes at a temperature of not more than 50° C. while cooling in ice. After stirring for a further 1 hour, the virtually clear solution is dispensed. The conversion of FACH is 99.2% according to Liebig titration. The reaction mixture comprises 0.07% of free hydrocyanic acid (determined by Volhard titration). Titration indicates an EDDN yield of 87.7% based on FACH used. EDMN cannot be determined by titration. Assuming that EDMN is formed from reacted ethylenediamine which does not react to form EDDN, the total amino nitrile yield is 93% and the yield of EDMN is thus 5%.

Triethylenetetramine

The subsequent hydrogenation of the solution obtained above is carried out continuously in a 270 ml autoclave provided with baffles and a disk stirrer. 22 g of a Cr-doped Raney cobalt are placed in the autoclave and 20 standard l of hydrogen are fed in continuously. 4.5 g of the EDDN solution together with 2 g of an internal standard, 4.9 g of EDA and 30 g of THF are fed in per hour. The hydrogenation is carried out at 120° C. and 100 bar. Over a period of 26 hours, an average of 2.6 by weight of Pip, 19.5% by weight of DETA as C4 products and 5.6% by weight of AEPip and 79.9% by weight of TETA as C6 products can be isolated. Based on EDDN, this corresponds to a yield of 96% of C6 products.

Example 7

Formaldehyde Cyanohydrin

FACH is prepared by variant b) of the general method.

Ethylenediaminediacetonitrile 120 g (2 mol) of EDA are placed in a 2 l reaction vessel and 340.8 g (4 mol) of FACH (67%) are added dropwise over a period of 30 minutes at a temperature of not more than 70° C. while cooling in ice. After stirring for a further 1 hour, the clear yellow-orange solution is dispensed. The conversion of FACH is 99.3% according to Liebig titration. The reaction mixture comprises 0.12% of free hydrocyanic acid (determined by Volhard titration). Titration indicates an EDDN yield of 91.6% based on FACH used. EDMN cannot be determined by titration. Assuming that EDMN is formed from reacted ethylenediamine which does not react to form EDDN, the total amino nitrile yield is 94.3% and the yield of EDMN is thus 3%.

Triethylenetetramine

The subsequent hydrogenation of the solution obtained above is carried out continuously in a 270 ml autoclave provided with baffles and a disk stirrer. 22 g of a Cr-doped Raney cobalt are placed in the autoclave and 20 standard l of hydrogen are fed in continuously. 4.5 g of the EDDN solution together with 2 g of an internal standard, 4.9 g of EDA and 30 g of THF are fed in per hour. The hydrogenation is carried out at 120° C. and 100 bar. Over a period of 26 hours, an average of 2.4% by weight of Pip, 13.2% by weight of DETA as C4 products and 4.8% by weight of AEPip and 84.1% by weight of TETA as C6 products can be isolated. Based on EDDN, this corresponds to a yield of 98% of C6 products.

Example 8

Influence of the Feed Rate in the Hydrogenation

In a separate trial, the influence of the feed rate only on the ratio of TETA/AEPip was examined.

Formaldehyde cyanohydrin

FACH is prepared by variant a) of the general method.

Ethylenediaminediacetonitrile 132 g (2.2 mol) of EDA are placed in a 2 l reaction vessel and 506.6 g (4 mol) of FACH (45% strength) are added dropwise over a period of 1.5 hours at a temperature of not more than 35° C. while cooling in ice. After stirring for a further 1 hour, a further 14.3 g (0.1 mol) of FACH (45% strength) are introduced and the mixture is heated to 40° C. A conversion of FACH of about 100% is obtained according to Liebig titration.
(EDDN Hydrogenation at Various Feed Rates)

3.25 g (dry) of a Cr-doped Raney cobalt catalyst and 15 ml of THF are placed in a 270 ml autoclave. The autoclave is heated to 120° C. and pressurized with hydrogen to a total pressure of 200 bar. 13.8 g of the aqueous EDDN solution obtained above, 13.8 g of an internal standard and 4.2 g of water in 106 g of THF are introduced over a defined period of time. The reaction mixture is stirred under the reaction conditions for a further 60 minutes. Samples are taken at different times and homogenized by means of methanol. After the addition is complete, no EDDN can be detected.

The ratio of TETA/AEPip is determined as
a) 60 min addition: TETA/AEPip: 2.2
b) 180 min addition: TETA/AEPip: 3.3
c) 180 min addition: TETA/AEPip: 4.5

At a hydrogenation temperature of 80° C. and an addition time of 60 min, a TETA/AE-Pip ratio of only 1.3 can be achieved.

Example 9

Ammonia as Additive

The EDDN solution obtained in example 7 is used for the hydrogenation in the presence of ammonia.
a) 3.25 g (dry) of a Cr-doped Raney cobalt catalyst, 15 ml of THF and 5.2 g of EDA are placed in a 270 ml autoclave. The autoclave is heated to 120° C. and pressurized with hydrogen to a total pressure of 200 bar. 13.8 g of the aqueous EDDN solution (43% by weight) obtained above, 13.8 g of an internal standard and 4.2 g of water in 106 g of THF are introduced over a period of 60 minutes. The reaction mixture is stirred under the reaction conditions for a further 60 minutes. Samples are taken at different times and homogenized by means of methanol. After the addition is complete, no EDDN can be detected. After an after-hydrogenation time of 60 minutes, the ratio of TETA to AEPip is 4.1.

In a further experiment, 12 g of ammonia is placed in the autoclave in addition to the EDA. This enabled the ratio to be increased to 9.0.
b) 3.25 g (dry) of a Cr-doped Raney cobalt catalyst, 15 ml of THF and 12 g of ammonia are placed in a 270 ml autoclave. The autoclave is heated to 120° C. and pressurized with hydrogen to a total pressure of 200 bar. 13.8 g of the aqueous EDDN solution (43% by weight) obtained above, 13.8 g of an internal standard and 4.2 g of water in 106 g of THF are introduced over a period of 60 minutes. The reaction mixture is stirred under the reaction conditions for a further 60 minutes Samples are taken at different times and homogenized by means of methanol. After the addition is complete, no EDDN can be detected. After an after-hydrogenation time of 60 minutes, the ratio of TETA to AEPip is 5.7.

The invention claimed is:

1. A process for preparing triethylenetetramine (TETA), which comprises hydrogenating ethylenediaminediacetonitrile (EDDN) in the presence of a catalyst and a solvent and at a pressure from 30 to 250 bar.

2. The process according to claim 1, wherein EDDN is present in an amino nitrile mixture comprising at least 30% by weight of EDDN and at least 5% by weight of ethylenediaminemonoacetonitrile (EDMN).

3. The process according to claim 1, wherein a Raney catalyst is used.

4. The process according to claim 3, wherein a skeletal Raney cobalt catalyst which has been obtained from a Co/Al alloy by leaching with aqueous alkali metal hydroxide solution and comprises at least one of the elements Fe, Ni or Cr as promoter is used.

5. The process according to claim 1, wherein the solvent is water or an organic solvent.

6. The process according to claim 5, wherein the organic solvent is tetrahydrofuran or methanol.

7. The process according to claim 1, wherein the pressure is from 40 to 160 bar or the temperature is from 70° C. to 140° C.

8. The process according to claim 2, wherein the amino nitrile mixture comprises from 10 to 25% by weight of EDMN.

9. The process according to claim 1, wherein TETA or diethylenetriamine (DETA) and optionally further ethylene amines which are comprised as by-products in the reaction product obtained in each case are isolated after the hydrogenation.

10. The process according to claim 2, wherein EDDN or EDMN is prepared by reaction of ethylenediamine (EDA) and formaldehyde cyanohydrin (FACH) or by reaction of EDA with formaldehyde and hydrocyanic acid.

11. The process according to claim 1, wherein the EDDN is fed to the hydrogenation at a rate which is not greater than the rate at which EDDN reacts with hydrogen in the hydrogenation.

12. The process according to claim 1, wherein the hydrogenation is carried out in the presence of an additive.

13. The process according to claim 12, wherein the hydrogenation is carried out in the presence of EDA or ammonia.

14. The process according to claim 6, wherein the pressure is from 40 to 160 bar and the temperature is from 70° C. to 140° C.

* * * * *